(12) United States Patent
Lopez et al.

(10) Patent No.: US 6,465,616 B1
(45) Date of Patent: Oct. 15, 2002

(54) INTERLEUKIN-5 ANTAGONIST

(75) Inventors: Angel Lopez, Medindie (AU); Matthew Vadas, Stirling (AU); Frances Shannon, Crafers (AU); Stan Bastiras, Adelaide (AU); Allan William Hey, Woodside (AU)

(73) Assignees: BresaGen Limited, Thebarton (AU); Medvet Science Pty. Ltd., Adelaide (AU)

(*) Notice: Subject to any disclaimer, the term of this patent is extended or adjusted under 35 U.S.C. 154(b) by 0 days.

(21) Appl. No.: 09/180,864

(22) PCT Filed: May 23, 1997

(86) PCT No.: PCT/AU97/00322

§ 371 (c)(1),
(2), (4) Date: Apr. 12, 1999

(87) PCT Pub. No.: WO97/45448

PCT Pub. Date: Dec. 4, 1997

Related U.S. Application Data

(63) Continuation-in-part of application No. 08/591,438, filed on Apr. 8, 1994, now Pat. No. 5,939,063.

(30) Foreign Application Priority Data

May 24, 1996 (AU) ............................................. PO0054

(51) Int. Cl.$^7$ ........................ C07K 14/00; A61K 38/00; A61K 38/04
(52) U.S. Cl. ............................. 530/350; 530/326; 514/2
(58) Field of Search ................................ 530/350, 326; 514/2

(56) References Cited

FOREIGN PATENT DOCUMENTS

| AU | B 6096090 | 2/1991 |
|----|-----------|--------|
| WO | WO 8304418 | 12/1983 |
| WO | WO 8910403 | 11/1989 |
| WO | WO 9307171 | 4/1993 |
| WO | WO 9412639 | 6/1994 |

OTHER PUBLICATIONS

Devos et al. Interleukin–5 and its receptor: a drug target for eosinophilia associated with chronic allergic disease. Journal of Leukocyte Biology. 1995. vol. 57, pp. 813–819.*
Tavernier et al. Identification of receptor–binding domains on human interleukin 5 and design of an interleukin–5–derived receptor antagonist. Proc. natl. Acad. Sci. USA. 1995. vol. 92, pp. 5194–5198.*
Graber et al. Identification of key charged residues of human interleukin–5 in receptor binding and cellular activation. J. Biol. Chem. 1995, vol. 270(26); pp. 15762–15769.*
Wells et al. Defining the regions of human interleukin–5 important in reeptor binding and cellular activation. Annals of the New York Acadamy of Science. 1996. vol. 796: pp. 226–234.*

Bazan, F., (1990) "Haempoetic receptors and helical cytokines", *Immunology Today*, 11(10):350–354.
Berndt, et al., (1994) "Mutagenic Analysis of a Receptor Contact Site of Interleukin–2: Preparation of an IL–2 Analog with Increased Potency+", *Biochemistry*, 33:6571–6577.
Brandhuber, et al., (1987) "Three–Dimensional Structure of Interleukin–2", *Science*, 238:1707–1709.
Burgess, et al., (1987) "Purification and Properties of Bacterially Synthesized Human Granulocyte–Macrophage Colony Stimulating Factor", *Blood*, 69(1):43–51.
Collins, et al., (1988) "Identification of specific residues of human interleukin 2 that affect binding to the 70–kDA subunit (p70) of the interleukin 3 receptor", *Proc. Natl. Acad. Sci. USA*, 85: 7709–7713.
Contreras, et al., (1983) "Iodine Monochloride (ICI) Iodination Techniques", *Methods Enzymol.*, 92:277–291.
Devos, et al., (1995) "Interleukin–5 and its receptor: a drug target for eosinophilia associated with chronic allergic disease", *Journal of Leukocyte Biology*, 57:813–819.
Dickason, et al., (1996) "Delineation of IL–5 Domains predicted to Engage the IL–5 Receptor Complex [1]", *The Journal of Immunology*, 56:1030–1037.
Elliott, et al., (1990) "IL–3 And Granulocyte–Macrophage Colony–Stimulating Factor Stimulate two Distinct Phases of Adhesion In Human Monocytes[1]", *The Journal of Immunology*, 145(1):167–176.
Gasson, et al., (1986) "High–affinity binding of granulocyte–macrophage colony–stimulating factor to normal and leukemic human myeloid cells", *Natl. Acad. Sci. USA*, 83:669–673.
Gearing, et al., (1989) "Expression cloning of a receptor for human granulocyte–macrophage colony–stimulating factor", *The EMBO Journal*, 18(12):3667–3676.
Ghrayeb, et al., (1984) "Secretion cloning vectors in *Escherichia coli*", *The EMBO Journal*, 3(10):2437–2442.
Goodall, et al., (1993) "A Model for the Interaction of the GM–CSF, IL–3 and IL–5 Receptors with their Ligands", *Growth Factors*, 8:87–97.
Gough, et al., (1984) "Molecular cloning of cDNA encoding a murine haematopoietic growth regulator, granulocyte–macrophage colony stimulating factor", *Nature*, 309:763–767.
Graber, et al., (1995) "Identification of Key Charged Residues of Human Interleukin–5 in Receptor Binding and Cellular Activation*", *The Journal of Biological Chemistry*, 270(26):15762–15769.

(List continued on next page.)

*Primary Examiner*—David S. Romeo
*Assistant Examiner*—Joseph F. Murphy
(74) *Attorney, Agent, or Firm*—Scully, Scott, Murphy & Presser

(57) ABSTRACT

The present invention relates to modified and variant forms of Interleukin-5 molecules capable of antagonizing or reducing the activity of IL-5 and their use in ameliorating, abating or otherwise reducing the aberrant effects caused by native or mutant forms of IL-5.

16 Claims, 11 Drawing Sheets

OTHER PUBLICATIONS

Figure 1A:
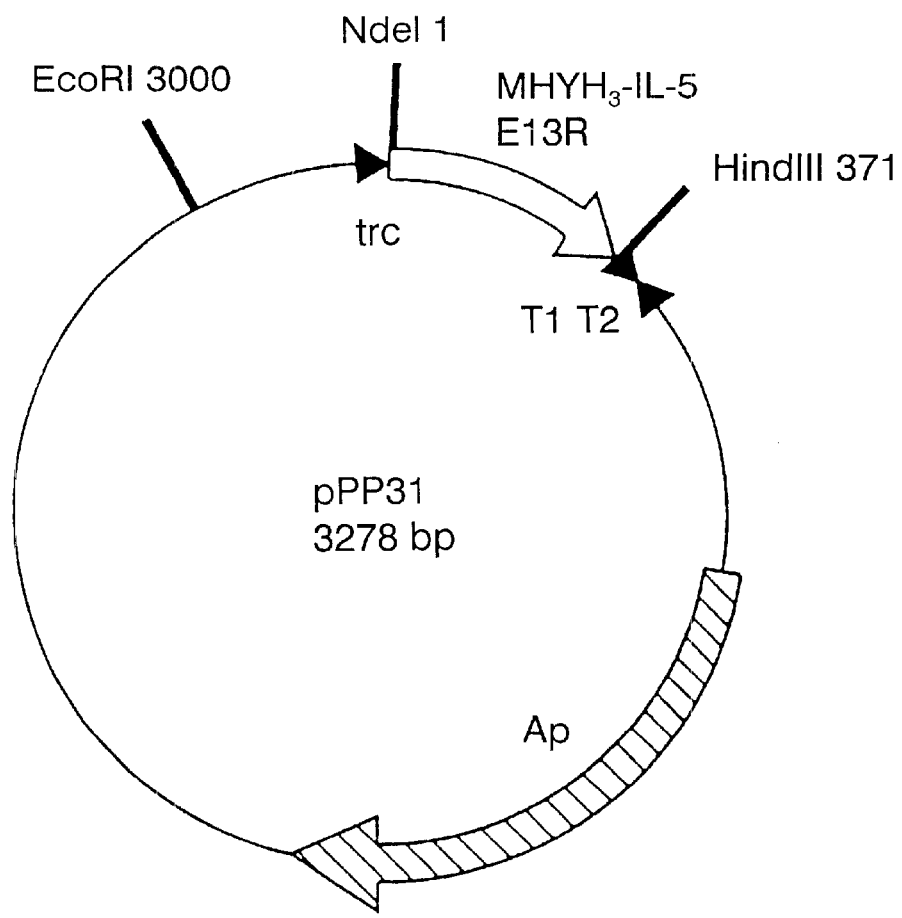

Hayashida, et al., (1990) "Molecular cloning of a second subunit of the receptor for human granulocyte–macrophage colony–stimulating factor (GM–CSF): Reconstitution of a high–affinity GM–CSF receptor", *Natl. Acad. Sci. USA*, 87:9655–9659.

Hercus, et al., (1994) "Specific human granulocyte–macrophage colony–stimulating factor antagonists", *Proc. Natl. Acad. Sci. USA*, 91:5838–5842.

Koshland, et al., (1980) "Secretion of Beta–Lactamase Requires the Carboxy End of the Protein", *Cell*, 20:749–760.

Kruse, et al., (1993) "Two distinct functional sites of human interleukin 4 are identified by variants impaired in either receptor binding or receptor activation", *The EMBO Journal*, 12(13):5121–5129.

Kuga, et al., (1989) "Mutagenesis of human granulocyte colony stimulating factor", *Biochem. and Biophys. Res. Comm.*, 159(1):103–1111.

Laemmli, U. K., (1970) "Cleavage of Structural Proteins during the Assembly of the Head of Bacteriophage T4", *Nature*, 227:680–685.

Lokker, et al., (1991) "Structure–Activity Relationship Study on Human Interleukin–3", *J. Biol. Chemistry*, 266(16):10624–10631.

Lopez, et al., (1986) "Recombinant Human Granulocyte–Macrophage Colony–stimulating Factor Stimulates In Vitro Mature Human Neutrophil and Eosinophil Function, Surface Receptor Expression, and Survival", *J. Clin. Invest.*, 78:1220–1228.

Lopez, et al., (1988) "Recombinant Human Interleukin–3 Stimulation of Hematopoiesis in Humans: Loss of Responsiveness With Differentiation in the Neutrophilic Myeloid Series", *Blood*, 72(5):1797–1804.

Lopez, et al., (1992) "Residue 21 of human granulocyte–macrophage colony–stimulating factor is critical for biological activity and for high but not low affinity binding", *The EMBO Journal*, 11:909–916.

Lopez, et al., (1992) "A human interleukin 3 analog with increased biological and binding activities", *Proc. Natl. Acad. Sci. USA*, 89:11842–11846.

Marston, F.A.O., (1987) "The purification of eukaryotic polypeptides expressed in *Escherichia coli*", In *DNA cloning: A practical approach*, 3:59–88.

Parry, et al., (1988) "Conformational Homologies among Cytokines: Interleukins and Colony Stimulating Factors", *J. of Mol. Recog.*, 1(3):107–110.

Morrissey, J. H., (1981) "Silver Stain for Proteins in Polyacrylamide Gels: A Modified Procedure with Enhanced Uniform Sensitivity", *Analytical Biochem.*, 117:307–310.

Proudfoot, et al., (1990) "Preparation and characterization of human interleukin–5 expressed in recombinant *Escherichia coli*", *Biochem. J.*, 270:357–361.

Reusch, et al., (1994) "Neutralizing monoclonal antibodies define two different functional sites in human interleukin–4", *Eur. J. Biochem.* 222:491–499.

Sambrook, et al., (1989) "Expressed of Cloned Genes in *Escherichia coli*", *Molecular Cloning*, 2ed., 17.37–17.43.

Towbin, et al., (1979) "Electrophoretic transfer of proteins from polyacrylamide gels to nitrocellulose sheets: Procedure and some applications", *Proc. Natl. Acad. Sci. USA*, 76(9):4350–4354.

Wong, et al., (1985) "Human GM–CSF: Molecular Cloning of the Complementary DNA and Purification of the Natural and Recombinant Proteins", *Science*, 228:810–815.

Zav'yalov, et al., (1990) "Theoretical conformational analysis of a family of α–helical immunocytokines", *Biochimica et Biophysica Acta*. 1041:178–185.

Zoller, et al., (1984) "Oligonucleotide–Directed Mutagenesis: A Simple Method Using Two Oligonucleotide Primers and a Single–Stranded DNA Template", *Laboratory Methods*, 3(6):479–488.

Zurawski, et al., (1989) "Mouse interleukin–2 structurefunction studies: substitutions in the first α–helix can specifically inactivate p70 receptor binding and mutations in the fifth α–helix can specifically inactivate p55 receptor binding", *EMBO Journal*, 8(9):2583–2590.

* cited by examiner

```
CAT ATG CAC TAT CAC CAT CAC ATC CCC ACA GAA ATT CCC ACA AGT GCA        48
    Met His Tyr His His His Ile Pro Thr Glu Ile Pro Thr Ser Ala
    1                   5                  10                  15

TTG GTG AAA CGT ACC TTG GCA CTG CTT TCT ACT CAT CGA ACT CTG CTG        96
Leu Val Lys Arg Thr Leu Ala Leu Leu Ser Thr His Arg Thr Leu Leu
                    20                  25                  30

ATA GCC AAT ACT GAG CTG AGG ATT CCT CCT CAT GTA CAT CGA AAA AAT        144
Ile Ala Asn Thr Glu Leu Arg Ile Pro Pro His Val His Arg Lys Asn
                    35                  40                  45

CAA CTG TGC GAA GAA ATT TTT CCT CAG GTG GGA GTA CCT ACA GAG CAC        192
Gln Leu Cys Glu Glu Ile Phe Pro Gln Val Gly Val Pro Thr Glu His
            50                  55                  60

CAA ACT TGC GTG AAG ATA ATC TTC GGC CTG ATA GGA AAA CTG AGT            240
Gln Thr Cys Val Lys Ile Ile Phe Gly Leu Ile Gly Lys Leu Ser
                65                  70                  75

TTA ATA AAG TAC CAA ATT TTC TGT GAG GAC TTC AAA AAC TTG TCC            288
Leu Ile Lys Tyr Gln Ile Phe Cys Glu Asp Phe Lys Asn Leu Ser
    80                  85                  90                  95

CGT CGT AAC GTA CAG ATC GAC TAC TTT GGA GAG GAA CTT GAA                336
Arg Arg Asn Val Gln Ile Asp Tyr Phe Gly Glu Glu Leu Glu
                100                 105                 110

GTA ATG AAC CGT ACC TGG ATC GAA TCC                                    377
Val Met Asn Arg Thr Trp Ile Glu Ser
        115                 120

TGATGAAGCT T
```

Fig. 1B

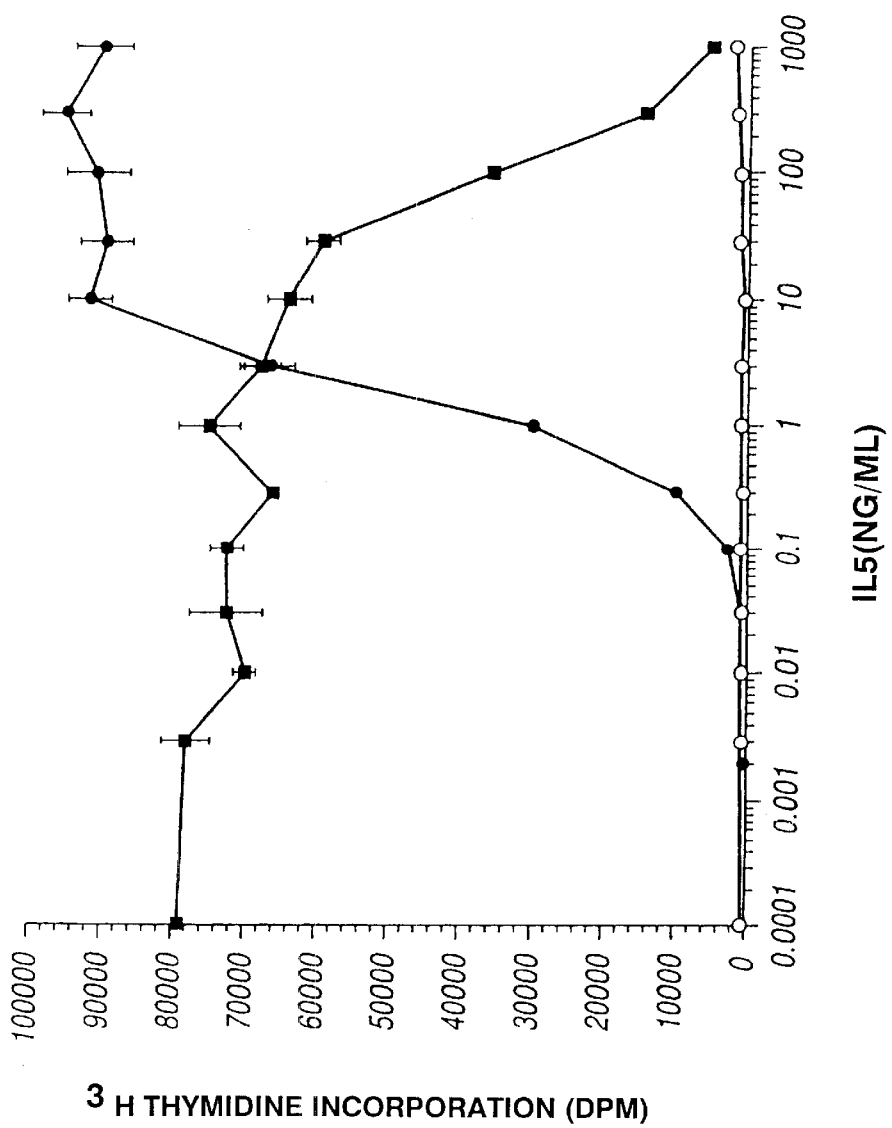

INTERLEUKIN-5 ANTAGONIST

CROSS REFERENCE TO THE RELATED PATENT APPLICATION

This application is a continuation-in-part application of Ser. No. 08/591,438, filed on Apr. 8, 1996 now U.S. Pat. No. 5,939,063.

The present invention relates to modified and variant forms of Interleukin-5 molecules capable of antagonizing or reducing the activity of IL-5 and their use in ameliorating, abating or otherwise reducing the aberrant effects caused by native or mutant forms of IL-5.

Sequence Identity Numbers (SEQ ID NOs.) for the nucleotide and amino acid sequences referred to in the specification are defined following the description.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The rapidly increasing sophistication of recombinant DNA technology is greatly facilitating research and development in the medical and allied health fields. This is particularly important in the area of haemopoietic growth factor research where a number of disease conditions are predicated on the aberrant effects of native or mutant forms of growth factors.

One particularly important haemopoietic growth factor is IL-5. This molecule is a lymphokine secreted by T-cells and mast cells and is a disulfide-linked homodimeric glycoprotein. The human form of this molecule comprises 114 amino acids per monomer. IL-5 consists of a bundle of four a-helices in an up-up, down-down array. The phenomenon of D-helix swapping whereby one bundle is built up of three helices coming from one monomer and a fourth helix which is contributed by the second monomer is unique to IL-5. The IL-5 molecule also contains two short anti-parallel β-strands located between helices A and B and helices C and D.

Human and murine IL-5 receptors comprise two different chains, the α and β-subunits.

Human IL-5 binds to the α-subunit but the binding affinity is increased upon association with the β-chain. The β-chain is shared by other cytokines such as GM-CSF and IL-3.

IL-5 is a haemopoietic growth factor with selectivity for production and activation of human eosinophils. There is a need, therefore, to develop antagonists of IL-5 to act as therapeutic agents for chronic asthma or other disease states with demonstrated eosinophilia or other conditions associated with IL-5. It is also important for the IL-5 antagonist not to interfere with the activities of other cytokines, such as GM-CSF or IL-3.

Accordingly, one aspect of the present invention contemplates a modified IL-5 comprising a sequence of amino acids within a first a-helix wherein one or more exposed amino acids in said first a-helix having acidic or acidic-like properties are substituted with a basic amino acid residue or a non-acidic amino acid residue.

The IL-5 which is subject to modification is generally of mammalian origin such as from humans, primates, livestock animals (eg. sheep, cows, pigs, horses), laboratory test animals (eg. mice, rats, guinea pigs, rabbits), companion animals (eg. dogs, cats) and captive wild animals (eg. kangaroos, foxes, deer). Most preferably, the IL-5 is of human origin. The modified IL-5 of the present invention may be glycosylated or unglycosylated and does not interfere with GM-CSF or IL-3 activity.

Even more particularly, the present invention is directed to a modified human IL-5 molecule comprising a sequence of amino acids wherein Glu at amino acid position 13 (or its equivalent position) in a first a-helix is replaced by Arg or Lys or a chemical equivalent or derivative thereof. An alternative substitution may also be made using non-acidic amino acid residues such as but not limited to Gln and Asn or their chemical equivalent or derivatives. A "derivative" may be a naturally occurring or synthetic amino acid residue.

In accordance with the present invention, it is proposed that the modified IL-5 molecules defined above act as antagonists of the native form of IL-5. The term "modified" is considered herein synonymous with terms such as "variant", "derivative" and "mutant". The present invention is particularly directed to a modified IL-5 which exhibits specific antagonism of IL-5 mitogenic effects such as observed in vitro. The modified IL-5 molecules may be glycosylated or unglycosylated and do not interfere with GM-CSF or IL-3 activity.

Accordingly, another aspect of the present invention is directed to an IL-5 antagonist said antagonist comprising an IL-5 molecule having an amino acid sequence in its first at-helix wherein one or more exposed amino acids in said first α-helix having acidic or acidic-like properties are substituted with a basic amino acid residue or a non-acidic amino acid residue.

More particularly, the present invention provides an antagonist of IL-5 said antagonist comprising an IL-5 molecule with Gln at position 13 (or its equivalent position) in a first α-helix substituted by Arg or Lys or a chemical equivalent or derivative thereof An alternatively substitution may also be made using non-acidic amino acid residues such as but not limited to Gln and Asn or their chemical equivalents or derivatives.

The modified IL-5 molecule of the present invention is preferably in recombinant or synthetic form and, with the exception of the amino acid substitution(s) in the first a-helix, the amino acid sequence of the IL-5 may be the same as the naturally occurring molecule (i.e. native molecule) or may carry single or multiple amino acid substitutions, deletions and/or additions to the native amino acid sequence. It is then referred to as a "mutant" IL-5. The structure of the first α-helix of IL-5 has been determined at 2.4 angstrom resolution by X-ray crystallography and comprises amino acid residues 7 to 27 or their equivalents (see Milburn et al. *Nature* 363: 172–176, 1993). The modified IL-5 of the present invention may or may not comprise a leader sequence.

The nucleotide and corresponding amino acid sequence for the modified IL-5 having Arg in position 13 is shown in SEQ ID NOs: 1 and 2 and FIG. 1. The leader sequence is shown as amino acids 1 to 6 (Met His Tyr His His His [SEQ ID NO:3]). Consequently, amino acids 7 to 27 are shown as amino acids 13–33 in SEQ ID NOs: 1 and 2 and in FIG. 1. Reference to amino acids 7 to 27 is taken as amino acid residue numbers in a molecule without a leader sequence. The amino acid sequence for amino acids 7 to 27 is shown as SEQ ID NO:4 except that amino acid 13 is represented as Xaa. In accordance with the present invention Xaa is preferably a basic amino acid residue or a non-acidic amino acid residue.

Reference to "unglycosylated form" herein means that the molecule is completely unglycosylated such as when expressed in recombinant form in a prokaryotic organism (e.g. *E. coli*). Alternatively, a glycosylation-deficient mammalian cell may be used or complete deglycosylation may occur in vitro using appropriate enzymes. Different glycosylation patterns are encompassed by the present invention such as when recombinant molecules are produced in different mammalian cells.

An "exposed" amino acid is taken herein to refer to an amino acid on a solvent-exposed or outer portion of an α-helix compared to those amino acids orientated towards the inside of the molecule.

An acidic amino acid includes, for example, Glu and Asp. Preferred basic amino acids are Arg and Lys. Preferred non-acidic amino acids are Gln and Asn.

According to another aspect of the present invention there is provided a modified IL-5 characterised by:
(i) comprising a sequence of amino acids within a first α-helix, (ii) having one or more exposed amino acids in said α-helix which have acidic or acidic-like properties being substituted by a basic amino acid residue or a non-acidic amino acid residue;

(iii) being in recombinant or synthetic form; and (iv) being capable of antagonising IL-5 mitogenic activity in vitro.

In a related embodiment, the present invention provides an IL-5 antagonist characterised by:

(i) comprising a sequence of amino acids within a first α-helix;

(ii) having one or more exposed amino acids in said α-helix which have acidic or acidic-like properties being substituted by a basic amino acid residue or a non-acidic amino acid residue;

(iii) being in recombinant or synthetic form; and (iv) being capable of antagonising IL-5 mitogenic activity in vitro.

The IL-5 mutant may be in glycosylated or unglycosylated form.

This aspect of the present invention is predicated in part on the finding that a mutation in amino acid 13 (Glu) of human (h) IL-5 to Arg results in the IL-5 variant being capable of antagonising IL-5 mitogenic effects in vitro. This variant is referred to herein as "IL-5 $Arg^{13}$" "E13 R". Such a variant would be unable to bind to high affinity receptors but would still able to fully bind the low affinity a chain of the IL-5 receptor. Importantly, the IL-5 $Arg^{13}$ mutant acts as an antagonist, preventing the stimulatory effect of native IL-5. A particularly important use of the IL-5 $Arg^{13}$ antagonist is in reducing or otherwise antagonising IL-5-mediated stimulation and activation of eosinophils in vivo or in vitro. The antagonist may also be able to antagonise effects caused by a mutated, endogenous IL-5. The present invention extends to a range of other IL-5 mutants such as IL-5 $Lys^{13}$, IL-5 $Gin^{13}$ and IL-5 $Asn^{13}$ as well as functionally equivalent mutants. The nucleotide and corresponding amino acid sequence for IL-5 $Arg^{13}$ (E13R) are shown in SEQ ID NOs: 1 and 2. The present invention extends, in a particularly preferred embodiment, to an isolated polypeptide having an amino acid sequence substantially as set forth in SEQ ID NO:2 or a genetic sequence encoding same having a nucleotide sequence substantially as set forth in SEQ ID NO:1.

By way of a shorthand notation, both single and three letter abbreviations are used for amino acid residues in the subject specification and these are defined in Table 1.

Where a specific amino residue is referred to by its position in IL-5, a single or three letter amino acid abbreviation is used with the residue number given in superscript (eg. wherein $Xaa^n$, wherein Xaa is the amino acid residue) and "n" is the residue number in the molecule.

TABLE 1

| Amino acid | Three-letter abbreviation | Corresponding single-letter abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention is exemplified using IL-5 $Arg^{13}$. This is done, however, with the understanding that the present invention extends to all other IL-5 variants having antagonistic properties to IL-5 in vitro or against eosinophils in vitro or in vivo.

According to another aspect of the present invention there is provided an IL-5 variant comprising an amino acid sequence in the first α-helix of said IL-5:

Thr Ser Ala Leu Val Lys Xaa Thr Leu Ala Leu Leu Ser Thr His Arg Thr Leu Leu lie Ala [SEQ ID No. 4];

wherein Xaa is a basic or non-acidic amino acid residue preferably selected from the group consisting of Arg, Lys, Gln and Asn and wherein said variant IL-5 acts as an antagonist for at least one property of the corresponding native IL-5. The amino acid sequence defined by SEQ ID NO:4 corresponds to amino acid residues 7 to 27 of human IL-5. Preferably, Xaa is $Xaa^n$ wherein n is amino acid position 13 of human IL-5. Preferably $Xaa^n$ is $Arg^{13}$ or its equivalent.

In a related embodiment, the present invention contemplates an IL-5 antagonist comprising a polypeptide or chemical equivalent thereof comprising amino acids 7 to 27 of the first α-helix of human IL-5 with the proviso that one or more exposed amino acids in said first α-helix having acidic or acidic-like properties are substituted by a basic amino acid residue or a non-acidic amino acid residue.

Preferably, the acidic or acidic-like amino acid residue if Glu or Asp and is replaced by Arg, Lys, Gln or Asn.

More preferably, the acidic or acidic-like amino acid residue is replaced by Arg.

Most preferably, the amino acid sequence of the modified IL-5 is as set forth in SEQ ID NO:2.

In a particularly preferred embodiment, the present invention is directed to an IL-5 antagonist comprising a modified IL-5 molecule having the following amino acid sequence in its first α-helix:

Thr Ser Ala Leu Val Lys Xaa Thr Leu Ala Leu Leu Ser Thr His Arg Thr Leu Leu Ile Ala [SEQ ID NO:4]

wherein Xaa is Arg;

or an IL-5 molecule having a single or multiple mutation in its first α-helix giving functionally similar antagonistic properties to the mutation wherein Xaa is Arg.

In respect of the latter embodiment, the mutation in the IL-5 molecule may be a single or multiple amino acid substitution, deletion and/or addition or may be an altered glycosylation pattern amongst other mutations. Preferably, the IL-5 antagonist comprises an amino acid sequence as set forth in SEQ ID NO:2.

The IL-5 antagonists of the present invention and in particular IL-5 Arg$^{13}$ are useful inter alia in the treatment of allergy, some myeloid leukemias (such as eosinophilic myeloid leukaemia), idiopathic eosinophilic syndrome, allergic inflammations such as asthma, rhinitis and skin allergies by preventing or reducing IL-5-mediated activation of eosinophils. These and other conditions are considered herein to result from or be facilitated by the aberrant effects of an endogenous native IL-5 or an endogenous naturally mutated IL-5.

The present invention, therefore, contemplates a method of treatment comprising the administration to a mammal of an effective amount of a modified IL-5 as hereinbefore defined and in particular IL-5 Arg$^{13}$ for a time and under conditions sufficient for effecting said treatment.

Preferably, the treatment is in respect of the treatment of allergy, some myeloid leukemias (such as eosinophilic myeloid leukaemia), idiopathic eosinophilic syndrome, allergic inflammations such as asthma, rhinitis and skin allergies.

Generally, the mammal to be treated is a human, primate, livestock animal, companion animal or laboratory test animal. Most preferably, the mammal is a human.

A single modified IL-5 may be administered or a combination of variants of the same IL-5. For example, a range of IL-5 variants could be used such as a combination selected from two or more of IL-5 Arg$^{13}$, IL-5 Lys$^{13}$, IL-5 Gln$^{13}$ and IL-5 Asn$^{13}$. The IL-5 present invention are particularly useful in treating eosinophilia and conditions resulting therefrom such as asthma. Administration is preferably by intravenous administration but a range of other forms of administration are contemplated by the present invention including via an implant device or other form allowing sustained release of the IL-5 variant, in a nebuliser form or nasal spray. Modified forms of IL-5 permit entry following topical application are also encompassed by the present invention.

In addition to the modifications to IL-5 contemplated above, the present invention further provides a range of other derivatives of IL-5.

Such derivatives include fragments, parts, portions, mutants, homologues and analogues of the IL-5 polypeptide and corresponding genetic sequence. Derivatives also include single or multiple amino acid substitutions, deletions and/or additions to IL-5 or single or multiple nucleotide substitutions, deletions and/or additions to the genetic sequence encoding IL-5. Derivatives also contemplated modifications to resident nucleotides. Alteration of the nucleotides may result in a corresponding altered amino acid sequence or altered glycosylation patterns amongst other effects. "Additions" to amino acid sequences or nucleotide sequences include fusions with other peptides, polypeptides or proteins or fusions to nucleotide sequences. Reference herein to "IL-5" includes reference to all derivatives thereof including functional derivatives or IL-5 immunologically interactive derivatives. All such derivatives would be in addition to the modifications to the first α-helix contemplated above. Accordingly, such derivatives would be to IL-5 Arg$^{13}$, IL-5 Lys$^{13}$, IL-5 Gln$^{13}$ or IL-5 Asn$^{13}$.

Analogues of IL-5 contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

The present invention further contemplates chemical analogues of IL-5 capable of acting as antagonists or agonists of IL-5 or which can act as functional analogues of IL-5. Chemical analogues may not necessarily be derived from IL-5 but may share certain conformational similarities. Alternatively, chemical analogues may be specifically designed to mimic certain physiochemical properties of IL-5. Chemical analogues may be chemically synthesised or may be detected following, for example, natural product screening.

Other derivatives contemplated by the present invention include a range of glycosylation variants from a completely unglycosylated molecule to a fully glycosylated molecule and from a naturally glycosylated molecule to molecules with an altered glycosylation pattern. Altered glycosylation patterns may result from expression of recombinant molecules in different host cells.

All these types of modifications may be important to stabilise the modified IL-5 molecules if administered to an individual or when used as a diagnostic reagent. The modifications may also add, complement or otherwise facilitate the antagonistic properties of the modified IL-5 molecules.

Reference herein to a "modified" IL-5, therefore, includes reference to an IL-5 with an altered amino acid sequence in the first α-helix as well as, where appropriate, a range of glycosylation variants, amino acid variations in other parts of the molecule, chemical modifications to the molecule as well as fusion molecules.

The present invention also provides a pharmaceutical composition comprising the modified IL-5 molecules as hereinbefore defined or combinations thereof.

Accordingly, the present invention contemplates a pharmaceutical composition comprising a a modified IL-5, said modified IL-5 comprising a sequence of amino acids with a first α-helix wherein one or more exposed amino acids in said first α-helix having acidic or acidic-like properties are substituted with a basic amino acid residue or non-acidic amino acid residue, said composition further comprising one or more pharmaceutically acceptable carriers and/or diluents.

In a related embodiment, the present invention provides a pharmaceutical composition comprising a modified human IL-5 or a mammalian homologue thereof said modified IL-5 comprising a sequence of amino acids in a first α-helix of:
Thr Ser Ala Leu Val Lys Xaa Thr Leu Ala Leu Leu Ser Thr His Arg Thr Leu Leu Ile Ala [SEQ ID NO:4]
wherein Xaa is a basic non-acidic amino acid residue preferably selected from Arg, Lys, Gln and Asn, said composition further comprising one or more pharmaceutically acceptable carriers and/or diluents. Preferably, Xaa is Xaa$^n$ where n is amino acid position 13. Preferably, Xaa is Arg.

In another related embodiment, the present invention contemplates a pharmaceutical composition capable of antagonising IL-5, said composition comprising a modified IL-5 having an amino acid sequence in its first α-helix:
Thr Ser Ala Leu Val Lys Xaa Thr Leu Ala Leu Leu Ser Thr His Arg Thr Leu Leu Ile Ala [SEQ ID NO:4]
wherein Xaa is selected from Arg, Lys, Gln and Asn.

Preferably, Xaa is Arg.

The pharmaceutical compositions may also contain other pharmaceutically active molecules including other IL-5 variants. The modified IL-5 molecule and other components in a pharmaceutical composition are referred to below as "active agents" or "active compounds".

The pharmaceutical forms suitable for injectable use include sterile aqueous solutions (where water soluble) or dispersions and sterile powders for the extemporaneous preparation of sterile injectable solutions or dispersions. It must be stable under the conditions of manufacture and storage and must be preserved against the contaminating action of microorganisms such as bacteria and fungi. The carrier can be a solvent or dispersion medium containing, for example, water, mannitol glycine or suitable mixtures thereof. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof. Mannitol glycine is a particularly useful formulation especially when the modified IL-5 molecules are given as an intravenous drip.

The present invention also extends to forms suitable for inhaling such as a nasal spray as well as in nebulizer form. Alternatively, sustained release compositions may be formulated as well as a range of implant devices. When suitably modified, the molecules may also be given as a cream, lotion or gel. A suitable carrier for a cream, lotion or gel includes a polyol such as but not limited to glycerol, propylene glycol, liquid polyethylene glycol and the like.

Pharmaceutically acceptable carriers and/or diluents include any and all solvents, dispersion media, and antibacterial and antifungal agents. The use of such media and agents for pharmaceutical active substances is well known in the art. Except insofar as any conventional media or agent is incompatible with the active ingredient, use thereof in the therapeutic compositions is contemplated by the present invention. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition involving or facilitated by aberration of IL-5 molecules or levels of IL-5.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of modulating modified IL-5 expression or modified IL-5 activity. The vector may, for example, be a viral vector.

Still another aspect of the present invention is directed to antibodies to the modified IL-5 molecules and their derivatives. Such antibodies may be monoclonal or polyclonal and may be specifically raised to modified IL-5 or derivatives thereof. In the case of the latter, a modified IL-5 or its derivatives may first need to be associated with a carrier molecule. The antibodies and/or recombinant modified IL-5 or its derivatives of the present invention are particularly useful as therapeutic or diagnostic agents.

For example, a modified IL-5 and its derivatives can be used to screen for naturally occurring antibodies to IL-5. These may occur, for example in some autoimmune diseases. Alternatively, specific antibodies can be used to screen for a modified or mutant IL-5. Techniques for such assays are well known in the art and include, for example, sandwich assays and ELISA. Knowledge of IL-5 levels may be important for diagnosis of certain cancers or a predisposition to cancers or for monitoring certain therapeutic protocols when modified IL-5 molecules are employed.

Antibodies to modified IL-5 of the present invention may be monoclonal or polyclonal. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regimen.

For example, specific antibodies can be used to screen for modified IL-5 proteins. The latter would be important, for example, as a means for screening for levels of modified IL-5 in a cell extract or other biological fluid or purifying modified IL-5 made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of modified IL-5.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of modified IL-5 or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting modified IL-5 in a biological sample from a subject said method comprising contacting said biological sample with an antibody specific for modified IL-5 or its derivatives or homologues for a time and under conditions sufficient for an antibody-modified IL-5 complex to form, and then detecting said complex.

The present invention also contemplates genetic assays such as involving PCR analysis to detect a modified IL-5 gene or its derivatives. Alternative methods include direct nucleotide sequencing or mutation scanning such as single stranded conformation polymorphism analysis (SSCP) as well as specific oligonucleotide hybridisation.

The present invention extends to nucleic acid molecules encoding a modified IL-5 of the present invention. Such nucleic acid molecules may be DNA or RNA. When the nucleic acid molecule is in DNA form, it may be genomic DNA or cDNA. RNA forms of the nucleic acid molecules of the present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli,* Bacillus sp and Pseudomonas sp. Preferred eukaryotic cells include yeast, fungal, mammalian and insect cells.

Accordingly, another aspect of the present invention contemplates a genetic construct comprising a vector portion and a mammalian and more particularly a human modified IL-5 gene portion, which modified IL-5 gene portion is capable of encoding an modified IL-5 polypeptide or a functional or immunologically interactive derivative thereof Preferably, the modified IL-5 gene portion of the genetic construct is operably linked to a promoter on the vector such that said promoter is capable of directing expression of said modified IL-5 gene portion in an appropriate cell.

In addition, the modified IL-5 gene portion of the genetic construct may comprise all or part of the gene fused to another genetic sequence such as a nucleotide sequence encoding glutathione-S-transferase or part thereof Accordingly, another aspect of the present invention contemplates an isolated nucleic acid molecule comprising a sequence of nucleotides encoding or complementary to a sequence encoding a modified IL-5, said modified IL-5 comprising a sequence of amino acids with a first α-helix wherein one or more exposed amino acids in said first α-helix having acidic or acidic-like properties are substituted with a basic amino acid residue or a non-acidic amino acid residue.

Preferably the sequence of nucleotides encodes a human modified IL-5 or a mammalian homologue which comprises a sequence of amino acids in a first α-helix of:

Thr Ser Ala Leu Val Lys Xaa Thr Leu Ala Leu Leu Ser Thr His Arg Thr Leu Leu Ile Ala [SEQ ID NO:4]
wherein Xaa is a basic or non-acidic amino acid residue preferably selected from Arg, Lys, Gln and Asn and wherein said modified IL-5 exhibits antagonism of IL-5 induced mitogenic effects. Preferably, Xaa is $Xaa^n$ where n is amino acid position 13. Preferably, Xaa is Arg.

The present invention extends to such genetic constructs and to prokaryotic or eukaryotic cells comprising same.

The present invention further contemplates the use of a modified IL-5 as hereinbefore defined in the manufacture of a medicament in the treatment of allergy, some myeloid leukemias (such as eosinophilic myeloid leukaemia), idiopathic eosinophilic syndrome, allergic inflammations such as asthma, rhinitis and skin allergies.

The present invention is further described by reference to the following non-limiting Examples and/or Figures.

In the Figures:

FIG. 1 is (a) a diagrammatic representation of the IL-5 E13R bacterial expression plasmid pPP31 and (b) DNA/amino acid sequence of $MHYH_3$-IL-5 (E13R). The E13R mutation is circled.

Figure 3A:
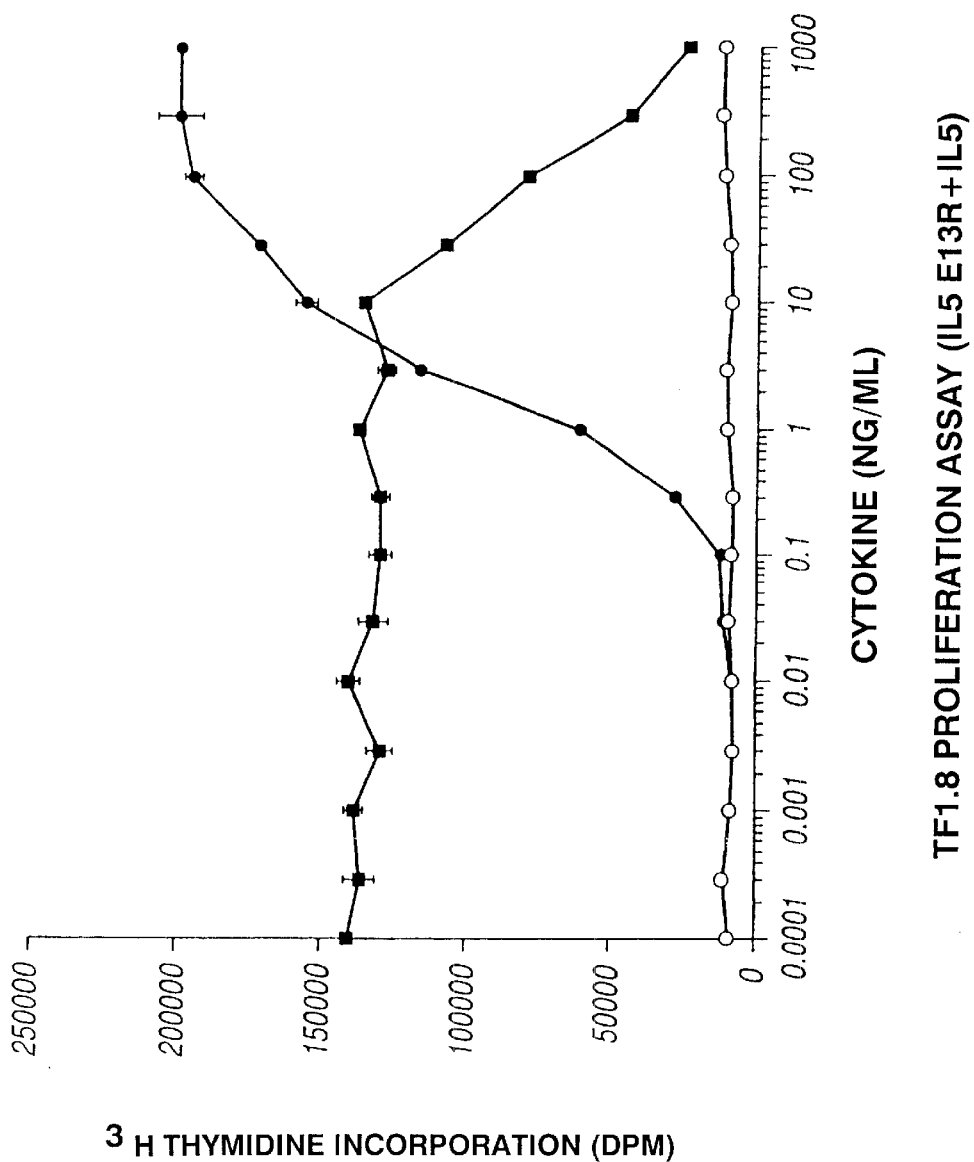
Figure 3B:
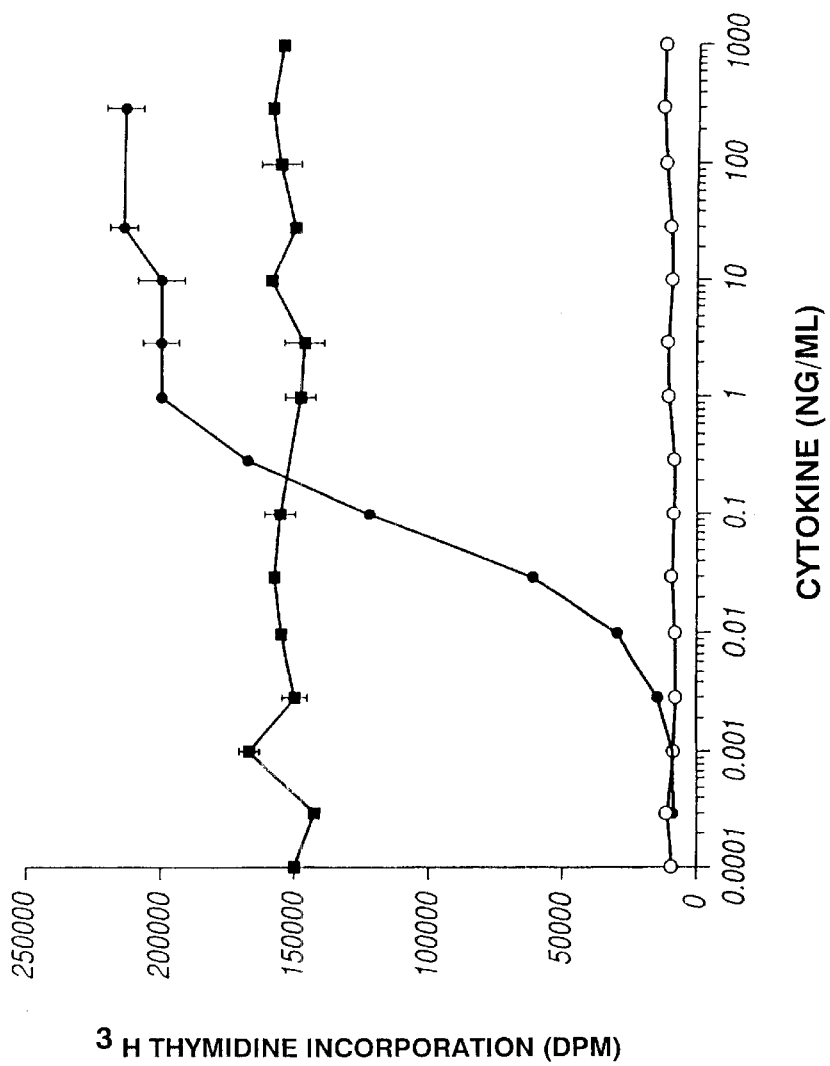
Figure 3C:
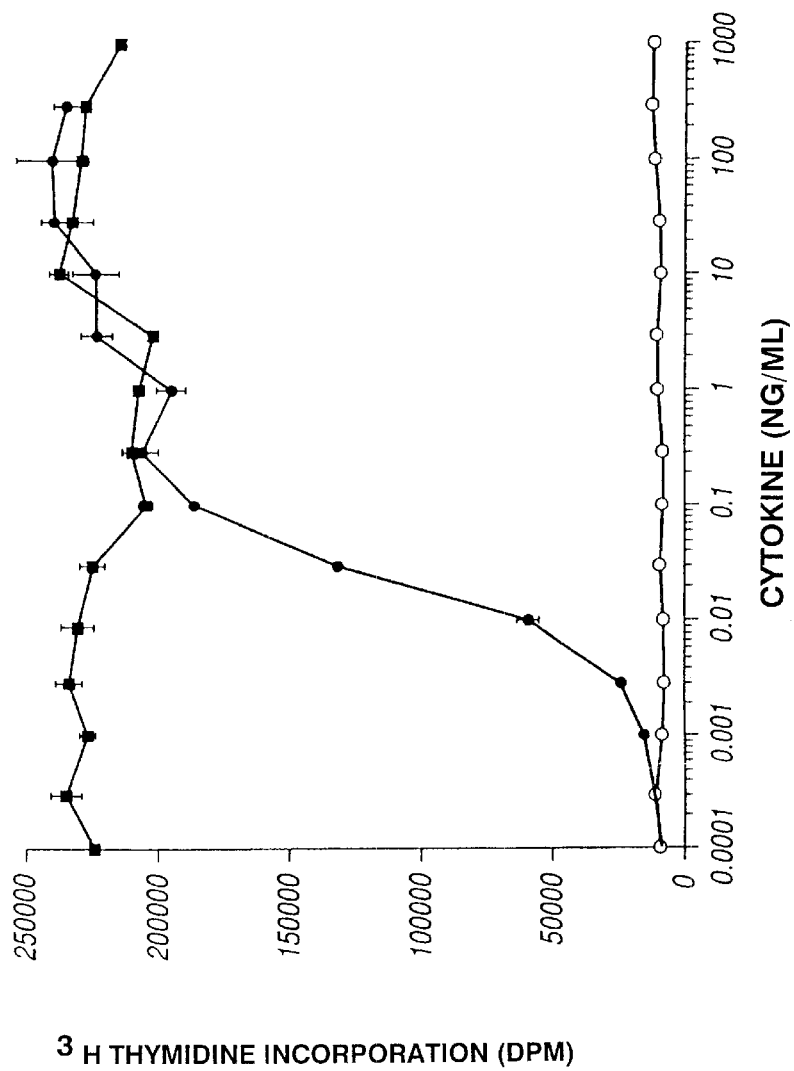
Figure 4:
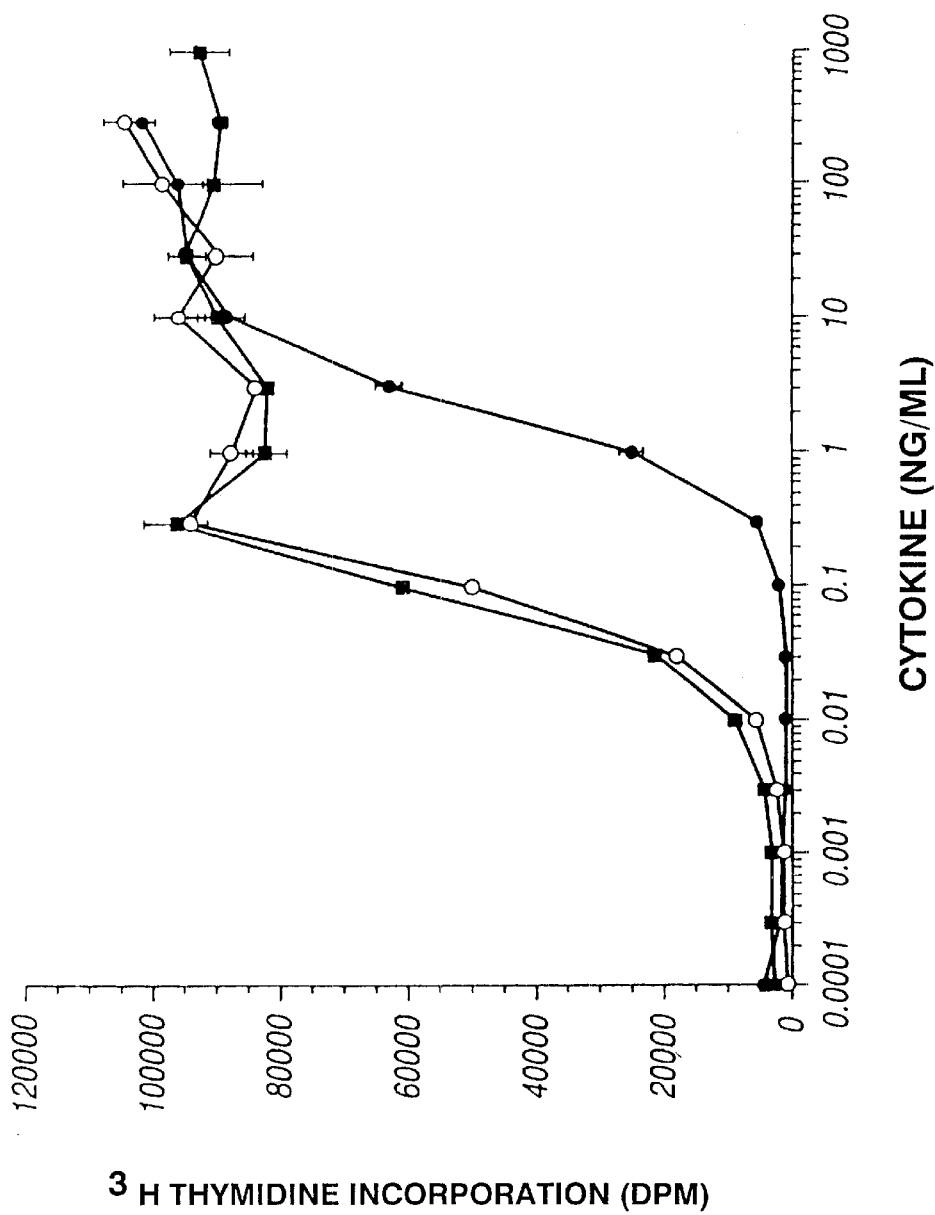

FIG. 2 is a graphical representation showing the titration E13R for its ability to antagonise IL-5-mediated proliferation of TF1.8 cells. IL-5 WT -o-IL-5 E13R -■-WT@ 3 ng/ml2+E13R FIG. 3A shows the titration of E13R for its ability to antagonise IL-5-mediated proliferation of TF1-8 cells. This figure also shows that E13R exhibits no detectable agonist activity. IL-5 WT -o-IL-5 E13R -■-IL-5+IL-5 E13R FIG. 3B shows the failure of E13R to antagonise IL-3-mediated proliferation of TF1.8 cells. IL-5 -o-IL-5 E13R -■-IL-3+IL-5 E13R FIG. 3C shows the failure of E 13R to antagonise GM-CSF-mediated proliferation of TF 1.8 cells. GM -o-IL-5 E13R -■-GM+IL-5E13R FIG. 4 is a graphical representation showing the titration of IL-3 for its mitogenic effects on TF1.8 cells and the failure of high levels of E13R to interfere with this activity. IL-5 WT -o-IL-3 -■-E13R@ 100 ng/ml+IL3

Figure 5:
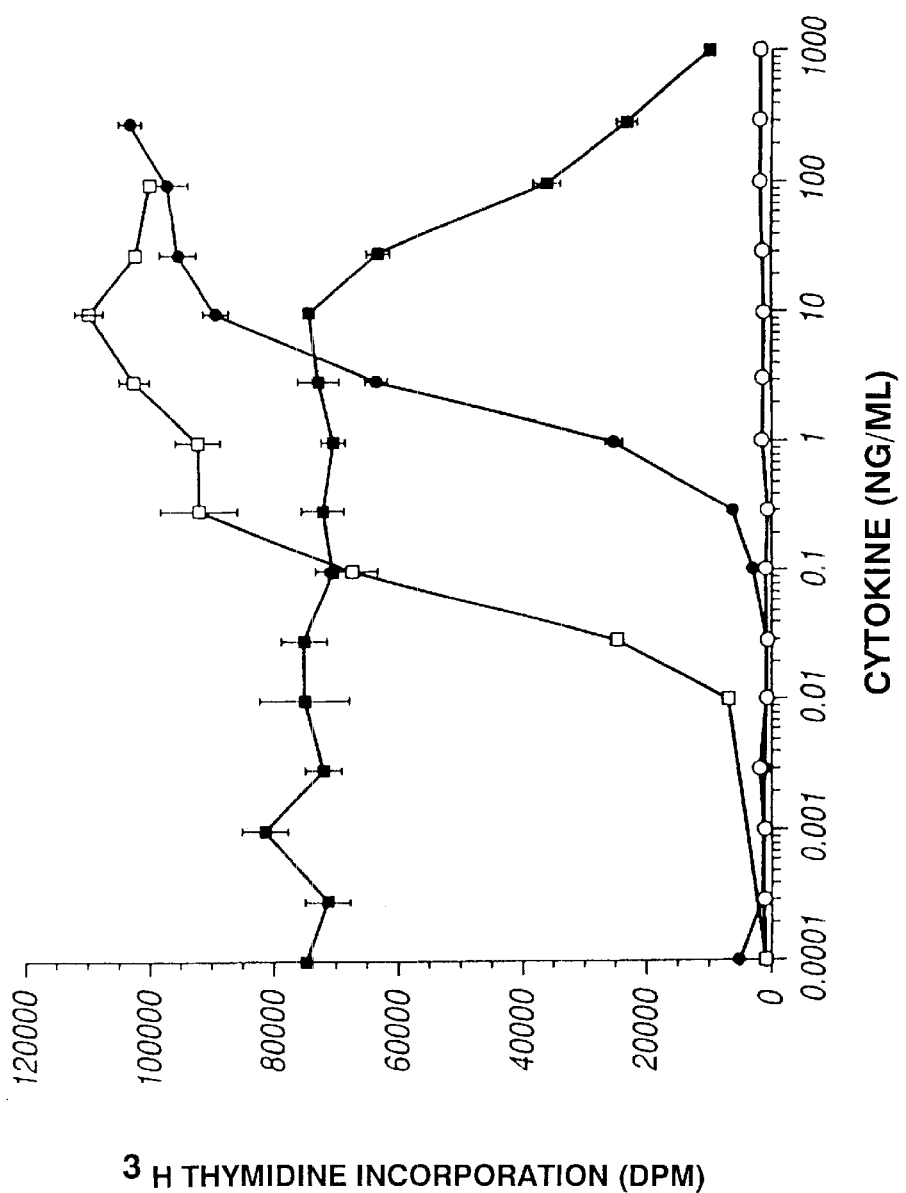

FIG. 5 is a graphical representation showing TF 1.8 proliferation assay for IL-5. IL-5 WT -o-IL-5E13R -■-WT IL5@ 3 ng/ml+E13R -□-WT IL5 (HI)

WT IL-5 (HI) was prepared in inclusion bodies in bacteria, dimerized in 2M urea, purified by reverse phase HPLC, concentrated in buffer exchange in PBS. It was never dried down.

IL-5 WT was prepared in the same way as WT IL-5 (HI) but after concentration, the preparation was dried down and dissolved in 25 mM glycine and 1.25 mg/ml of mannitol.

Figure 6:
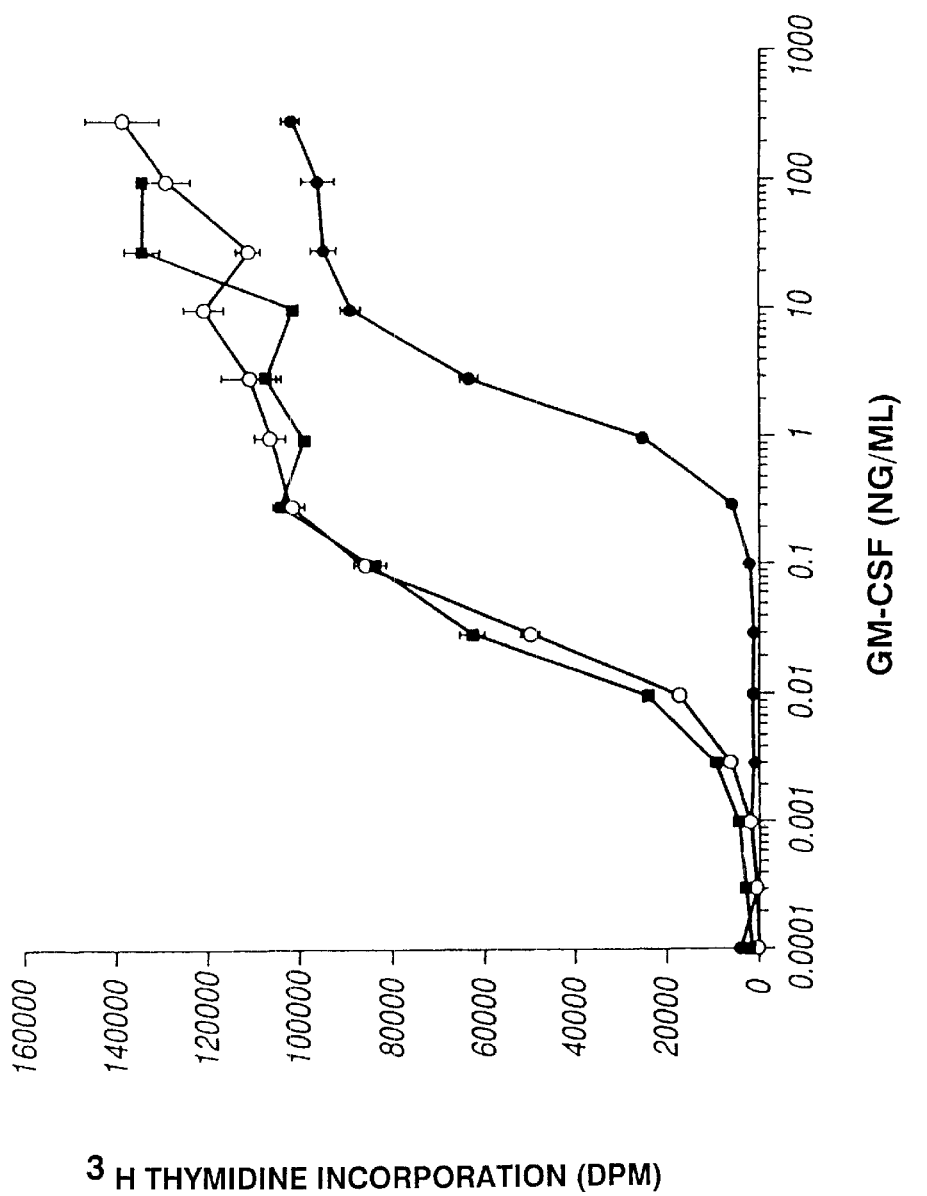
Figure 7:
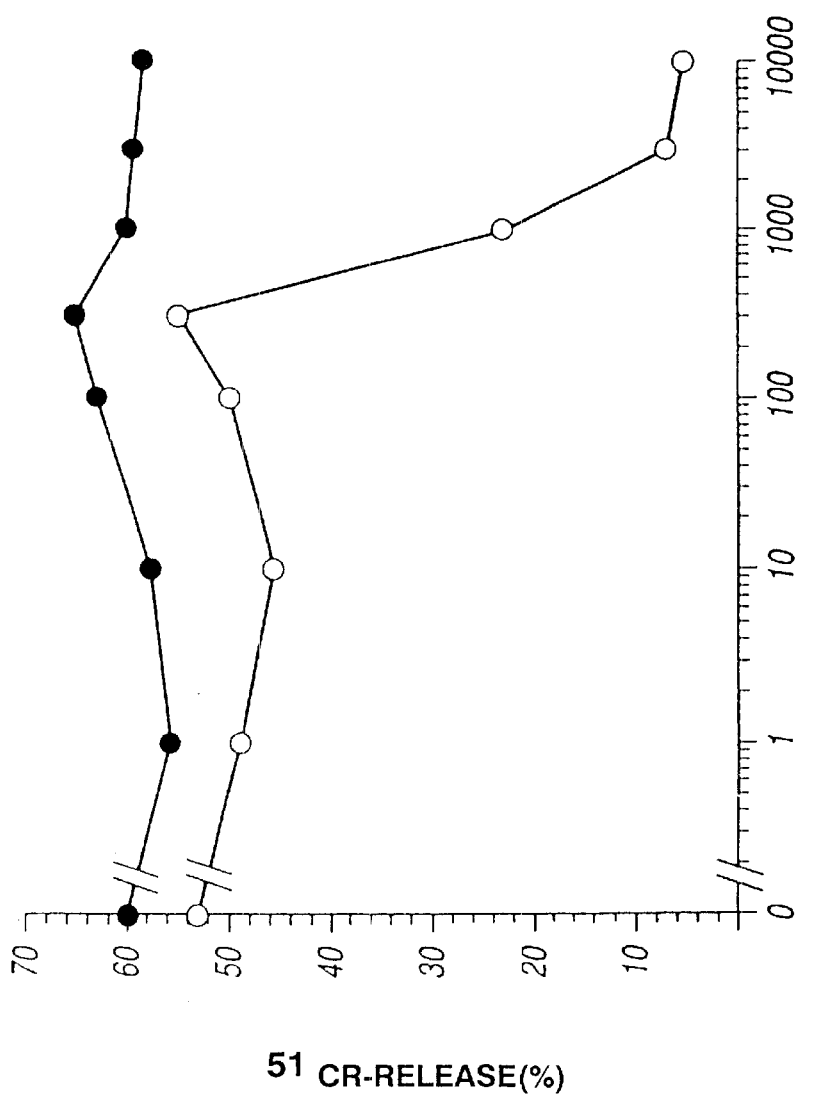

FIG. 6 is a graphical representation showing the titration of GM-CSF for its mitogenic effects on TF1.8 cells and the failure of high levels of E13R to interfere with this activity. IL-5 WT -o-GM -■-E13R@ 1000 ng/ml+GM FIG. 7 is a graphical representation showing that E13R inhibits IL-5 induced eosinophil antibody-dependent cell-mediated cytotoxicity. -o-E13R+IL-5 E13R+GM-CSF In the absence of GM-CSF and IL-5, the $\%^{51}Cr$-release was 4%.

Figure 8:
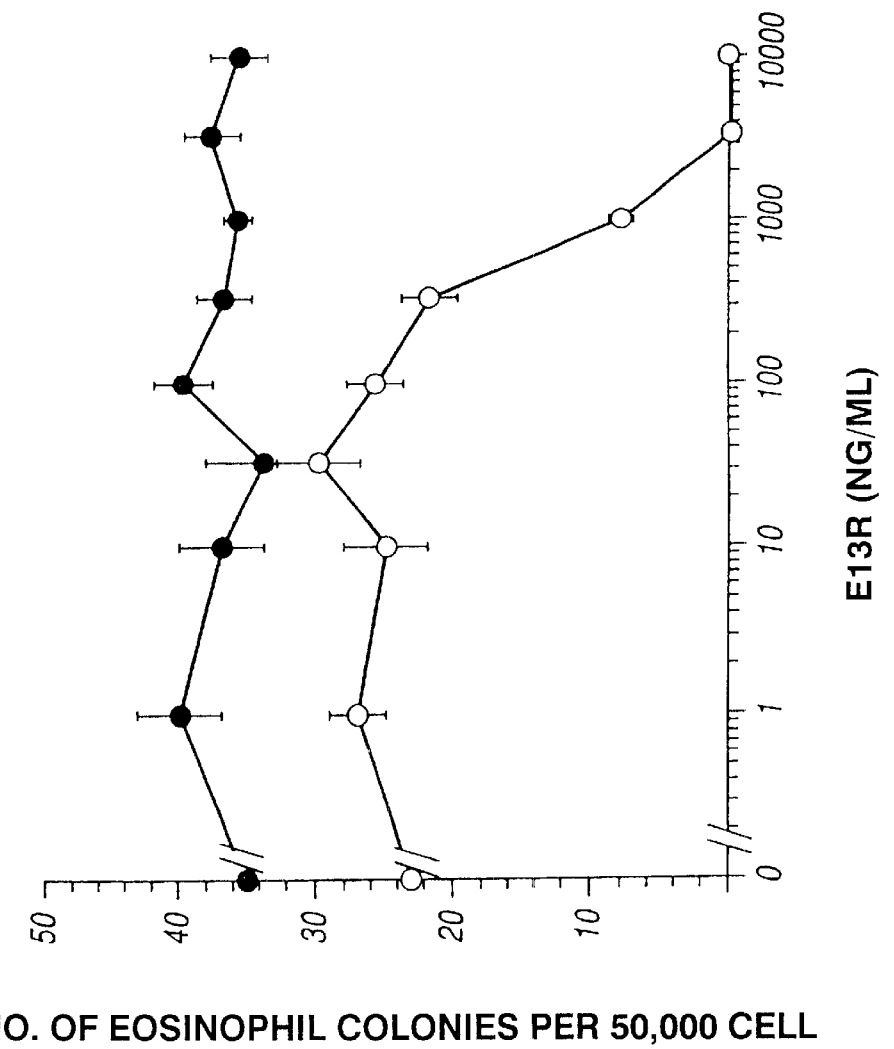

FIG. 8 is a graphical representation showing that E13R inhibits IL-5 induced eosinophil colony formation. -o-E13R+IL-5 -o-E13R+GM-CSF No eosinophil colonies were detected absent of GM-CSF and IL-5.

EXAMPLE 1

Production of a Charge-reversal Mutant of Interleukin 5(IL-5) with IL-5-antagonistic Properties The inventors expressed and purified a charge-reversal mutant of IL-5 in which the glutamate residue at position 13

(E13) is replaced by an arginine residue (R) [E13R]. This mutant, E13R, shows specific antagonism of IL-5 mitogenic effects in vitro. In order to maximise expression, this protein is presently being expressed as a fusion protein with the leader sequence $MHYH_3$ (MHYHHH) [SEQ ID NO:3]. The leader sequence comprises amino acids 1 to 6 in SEQ ID NOs: 1 and 2. However, there is no reason to believe that removal of this leader sequence (or its replacement by another leader sequence) will affect the antagonistic effects of E13R. A diagrammatic representation of $MHYH_3$ and the sequence of E13R is shown in FIG. 1. The nucleotide and corresponding amino acid sequence of E13R is represented in SEQ ID NOs: 1 and 2.

EXAMPLE 2

Production of a Bacterial Expression Plasmid Encoding $MHYH_3$IL-5 (E13R)

Human IL-5 E13R mutant coding sequence was derived from IL-5 wild-type sequence, by site-specific mutagenesis.

Codon 13 was changed to an Arg codon
CAG⇒CGT

The additional codon changes listed here were based on bacterial codon preferences to promote translational efficiency in *E. coli,* and did not lead to amino acid changes.

codon 82: CAA⇒CAG
codon 83: AAA⇒AAG
codon 84: AAA⇒AAG
codon 90: AGA⇒CGT
codon 91: CGG⇒CGT
codon 92: AGA⇒CGT
codon 97: CTA⇒CTG
codon 110: GAG⇒GAA
codon 112: ATA⇒ATC
codon 113 ATA⇒ATC
codon 115 AGT⇒TCC.

The mutant DNA fragment was modified by polymerase chain reaction using primers to generate a sequence encoding the leader $MHYH_3$ at the 5' end, and a stop codon at the 3' end. The amplified fragment was subcloned into the plasmid pEC611 to generate the expression plasmid pPP31, containing the trc promoter.

EXAMPLE 3

Production, Isolation and Refolding of $MHYH_3$ IL-5 (E13R)

Fermentation is by the Fed-Batch method. *Escherichia coli* MM294/pACYCLacI$^q$ transformed with the E13R-expressing plasmid pPP31 is grown in minimal medium at 37° C. The pH is held constant at pH 7.0 during bacterial growth by the addition of $NH_4OH$. Expression of IL-5 (E13R) is induced at high cell density ($OD_{600}$>20) either by addition of IPTG or by feeding with lactose. Induction continues for 5 hours (not including lag phase) with the protein being expressed as insoluble inclusion bodies (IBs). Cells are lysed by high pressure homogenization. A primary separation of IBs from cellular debris is done by differential centrifugation, after which the IBs are washed and homogenized one more time. A final centrifugation step isolates IBs of sufficient cleanliness for refolding.

The conditions for fermentation, induction, isolation and refolding are as follows:

1. FERMENTATION

A. Inoculation

1. *Escherichia coli* MM294/pACYClacI$^q$ carrying pPP3 1 was streaked out from a 80° C. glycerol stock onto a minimal medium plate containing ampicillin (100 μg/ml) and kanamycin (30 μg/ml) and grown overnight at 37° C.
2. Multiple colonies were assessed for IL-5 (E13R) expression levels by microscopic examination of 20 ml shake flask cultures containing inducer, or by colony size on agar plates with or without inducer, in this instance with IPTG.
3. The selected single colony from an agar plate was transferred into 20 ml of nitrogen-rich minimal medium (2) containing amplicillin (100 μg/ml)+kanamycin (30 μg/ml). The culture was grown at 37° C. overnight with agitation.
4. An amount of 10 L of C2 was sterilised in a 22 L fermenter and inoculated to a very low density with overnight culture. Growth was at 37° C. and a pH of 7.0 was maintained by the addition of $NH_4OH$ or $H_2SO_4$.
5. Agitation was manually controlled and aeration automatically controlled with oxygen saturation levels remaining above 10% v/v $pO_2$. Following depletion of glucose at 16–20 hours the cell mass was fed with a concentrated glucose solution containing additional salts. Nutrient feed flow rate was determined by pH or oxygen saturated levels.

B. Induction

1. At an optical density of $A_{600}$=>20 the recombinant expression of E13R antagonist was induced, in this instance by changing to a lactose based nutrient feed. Induction continued for 5 hours at 37° C., pH 7.0. Samples were removed at immediately preceding induction and each hour post-induction and examined by microscopy for the presence of IB, their size being determined by disc centrifugation.
2. The culture was stored overnight at 4° C.

2. PRIMARY ISOLATION OF IL-5 (E13R) INCLUSION BODIES

1. Homogenization—Step 1

The culture was passed five times through a Gaulin 30CD homogenizer at 13,500 psi, with homogenate being cooled between passes. Homogenate was then diluted with an equal volume of RO $H_2O$.

The IB size was redetermined by disc centrifugation.

2. Centrifugation—Step 1

The homogenate was centrifuged in a Westfalia SB-7 separator with a constant speed of 9,210 rpm at a flow rate determined by IB size.

The concentrate collected from this first step was diluted to ≦2.5% w/v.

3. Homogenization—Step 2

The IB suspension was passed once through a Gaulin 30CD homogenizer at 13,500 psi.

The IB size was again determined by disc centrifugation.

4. Centrifugation—Step 2

The homogenate was centrifuged in a Westfalia SA-1 separator with a constant speed of 9,700 rpm at a flow rate determined by IB size.

For refolding, IBs are initially dissolved in 6M Guanidine-HCl, containing 5–10 mM dithiothretiol and buffered to pH 9.5. Reduced IL-5 monomers of $MHYH_3$IL-5(E13R) are then purified from non-reduced protein by Size Exclusion Chromatography (eg. Superose 12 [Pharmacia]) in 6M Guanidine-HCl, containing 5mM dithiothreitol and buffered to pH 9.5. The purified reduced monomer is then refolded into dimers by dilution into 2M urea buffered to pH 9.5 at a final protein concentration of 0.01–0.1 mg/ml. Purification of correctly folded dimers is by reversed phase chromatography on a High Performance Liquid Chromatograph (HPLC) using a suitable column (eg. Brownlee butyl-silica employing 0.1% v/v trifluoroacetic acid (TFA) in water as Buffer A and 0.1% v/v TFA in acetonitrile as Buffer B). Purified, correctly folded protein can be recovered in biological buffers after lyophilization from HPLC buffers in the presence of mannitol and glycine, added as bulking excipient agents. The identity of the purified protein can be confirmed using mass spectrometry and N-terminal sequencing.

EXAMPLE 4

Assay for IL-5-antagonistic Activity

The biological assay for IL-5 antagonism by E13R uses incorporation of radiolabelled thymidine to detect IL-5-induced cellular proliferation. The cell line used, TF1.8, is a subline of TF1, a human erythroleukemic cell line which expresses the receptors for IL-3 and GM-CSF. TF1.8 differs from TF1 in that it has been selected for expression of the IL-5 receptor. Stimulation of TF1.8 proliferation by IL-5 is inhibited by 50% in the presence of a 30-fold excess of E13R, and abolished in the presence of a 300-fold excess (FIG. 2). However, stimulation of TF1.8 proliferation by IL3 or GM-CSF is unaffected by the presence of E13R. These results demonstrate that E13R is a specific and potent antagonist of IL-5. The $^3$H-thymidine assay was conducted as follows:

Wash cells 24 hrs, prior to assay (1500 rpm/5 min/RT) and resuspend them in cytokine free medium.

Dilute standards and samples to concentrations required, in culture medium mentioned above (range between 1000 ng/m–1 pg/ml as example). Dilutions were done in triplicate.

Aliquot dilutions of appropriate standards (GM-CSF, IL-3, IL-5, etc.) and samples in 100 ul final volumes, in sterile 96 well, flat bottom microtitre plates.

Check viability of washed cells and resuspend cells to a concentration of $5\times10^4$ cells/well.

Each cell contains 300 ul of diluted standard/sample+100 ul resuspended cells.

Plates are incubated @ 37° C. for 72 hrs, in a humidified $CO_2$ incubator (48 hrs, for TF-1 & TF1.8 cells).

Pulse cells with $^3$H-Thymidine (1/20 dilution of stock, then add 10 ul/well) 0.5 uCl/well.

Incubate plates @ 37° C. for 5 hrs in a humidified $CO_2$ incubator.

Harvest contents of each well onto filterpaper using cell harvester and determine the radioactivity incorporated into the DNA, by liquid scintillation counting.

The results are shown in FIGS. 2 to 6. The results show that E13R specifically antagonises IL-5 activity but does not interfere with GM-CSF or IL-3 activity. In particular, the Figures show that E13R does not antagonise TF1.8 cell proliferation induced by IL-3 nor does it antagonise TF1.8 cell proliferation induced by GM-CSF.

EXAMPLE 5 hIL-5 Lys$^{13}$

Thr Ser Ala Leu Val Lys Lys Thr Leu Ala Leu Leu Ser Thr His Arg Thr Leu Leu Ile Ala [SEQ ID NO. 5]

EXAMPLE 6 hIL-5 Arg$^{13}$

Thr Ser Ala Leu Val Lys Gln Thr Leu Ala Leu Leu Ser Thr His Arg Thr Leu Leu Ile Ala [SEQ ID NO. 6]

EXAMPLE 7 hIL-5 Gln$^{13}$

Thr Ser Ala Leu Val Lys Gln Thr Leu Ala Leu La Ser Thr His Arg Thr Leu Leu Ile Ala [SEQ ID NO. 7]

EXAMPLE 8 hIL-5 Asn$^{13}$

Thr Ser Ala La Val Lys Asn Thr Leu Ala Leu Leu Ser Thr His Arg Thr Leu Leu Ile Ala [SEQ ID NO. 8]

EXAMPLE 9

Antagonistic Properties of E13R on Eosinophils

An antibody dependent cell-mediated cytotoxicity (ADCC) assay was used to determine the effect of E13R on eosinophil function. This assay measures the ability of eosinophils to kill target cells radiolabelled with chromium and expressing a certain antibody recognized by the eosinophils (Vadas et al. *J Immunol* 130: 795, 1983). Blood was collected from a healthy donor and eosinophils were prepared by metrizamide gradient separation of leukocytes after removal of red cells with dextran (Vadas et al. *J Immunol* 122: 1228, 1979). The eosinophil purity exceeded 95%. The eosinophils were then incubated with the target cells at a ratio of 100 eosinophils per target cell, and a fixed dose of either GM-CSF (10 ng/ml) or IL-5 (10 ng/ml) and a titration of E13R. FIG. 7 shows that E13R dose-dependently antagonised IL-5-induced ADCC, but had no effect on GM-CSF-induced ADCC. Values are mean and sem of triplicates.

EXAMPLE 10

Effect of E13R on Proliferation and Differentiation of Eosinophilic Progenitors

Bone marrow was collected from a healthy donor and subjected to density centrifugation (Lymphoprep.). The mononuclear cells were plated in agar supplemented with a fixed dose of either GM-CSF (10 ng/ml) or IL-5 (10 ng/ml) and a titration ofE13R. The cells were allowed to grow at 37° C. for 2 weeks. The agar plates were then fixed in gluteraldehyde before the plates were stained with Luxol Fast Blue to detect eosinophilic colonies. FIG. 8 shows that E13R dose-dependently antagonized the colony-promoting effects of IL-5, while E13R had no effect on GM-CSF stimulation of eosinophilic colony formation. Values are mean and sem of triplicates.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. An isolated modified interleukin-5 (IL-5) comprising a sequence of amino acids with a first α-helix wherein at least one of the exposed amino acids in said first α-helix having acidic or acidic-like properties are substituted with a basic amino acid residue or a non-acidic amino acid residue selected from the group consisting of Arg, Lys and Asn, and wherein said modified IL-5 acts as an antagonist of IL-5.

2. An isolated modified human IL-5 comprising a sequence of amino acids in a first α-helix of: Thr Ser Ala Leu Val Lys Xaa Thr Leu Ala Leu Leu Ser Thr His Arg Thr Leu Leu Ile Ala (SEQ ID NO: 4) wherein Xaa is a basic or non-acidic amino acid residue selected from the group consisting of Arg, Lys, and Asn and wherein said modified IL-5 is an antagonist of IL-5.

3. An isolated IL-5 antagonist which antagonizes native human IL-5, comprising a modified IL-5 molecule wherein the amino acid residue at position 13 of the mature portion of said modified IL-5 is a basic amino acid residue or a non-acidic amino acid residue selected from the group consisting of Arg, Lys, and Asn.

4. An isolated IL-5 antagonist comprising the amino acid sequence as set forth in SEQ ID NO: 2 or the mature portion of SEQ ID NO: 2.

5. A pharmaceutical composition comprising a modified IL-5, which antagonizes native human IL-5, said modified IL-5 comprising a sequence of amino acids with a first α-helix wherein at least one of the exposed amino acids in said first α-helix having acidic or acidic-like properties are substituted with a basic amino acid residue or non-acidic amino acid residue selected from the group consisting of Arg, Lys and Asn, suad composition further comprising at least one of a pharmaceutically acceptable carrier or diluent.

6. A pharmaceutical composition comprising (i) a modified human IL-5 which inhibits native human IL-5 and comprises a sequence of amino acids in a first α-helix of: Thr Ser Ala Leu Val Lys Xaa Thr Leu Ala Leu Leu Ser Thr His Arg Thr Leu Leu Ile Ala (SEQ ID NO: 4), wherein Xaa is a basic or non-acidic amino acid residue selected from the group consisting of Arg, Lys and Asn; and (ii) at least one of a pharmaceutically acceptable carrier or diluent.

7. A pharmaceutical composition comprising: (i) a modified IL-5 which antagonizes native human IL-5 and comprises the amino acid sequence as set forth in SEQ ID NO:2 or the mature portion of SEQ ID NO: 2; and (ii) at least one of a pharmaceutically acceptable carrier or diluent.

8. The pharmaceutical composition according to claim 6 wherein Xaa of the IL-5 is Arg.

9. The pharmaceutical composition according to claim 6 wherein Xaa of the IL-5 is Lys.

10. The pharmaceutical composition according to claim 6 wherein Xaa of the IL-5 is Asn.

11. A method of preventing or reducing IL-5 mediated activation of eosinophils or antibody-dependent cell mediated cytotoxicity (ADCC) in a mammal comprising administering to said mammal an effective amount of a modified IL-5 for a time and under conditions sufficient to antagonize a native IL-5 in said mammal thereby preventing or reducing IL-5 mediated activation of eosinophils or ADCC, said modified IL-5 comprising a sequence of amino acids within a first α-helix wherein at least one of the exposed amino acids in said first α-helix having acidic or acidic-like properties are substituted with a basic amino acid residue or a non-acidic amino acid residue selected from the group consisting of Arg, Lys and Asn.

12. The method according to claim 11 wherein the IL-5 subject to modification is human IL-5.

13. A method of preventing or reducing IL-5 mediated activation of eosinophils or antibody-dependent cell mediated cytotoxicity (ADCC) in a mammal comprising administering to said mammal an effective amount of a modified human IL-5 for a time and under conditions sufficient to antagonize a native IL-5 in said mammal thereby preventing or reducing IL-5 mediated activation of eosinophils or ADCC, said modified IL-5 comprising a sequence of amino acids in a first α-helix of: Thr Ser Ala Leu Val Lys Xaa Thr Leu Ala Leu Leu Ser Thr His Arg Thr Leu Leu Ile Ala (SEQ ID NO: 4) wherein Xaa is a basic or non-acidic amino acid residue selected from the group consisting of Arg, Lys, and Asn.

14. The method according to claim 13 wherein the Xaa of the IL-5 is Arg.

15. The method according to claim 13 wherein the Xaa of the IL-5 is Lys.

16. The method according to claim 13 wherein the Xaa of the IL-5 is Asn.

* * * * *

SEQUENCE LISTING

<160> NUMBER OF SEQ ID NOS: 8

<210> SEQ ID NO 1
<211> LENGTH: 377
<212> TYPE: DNA
<213> ORGANISM: nucleotide sequence encoding modified IL-5
<220> FEATURE:
<221> NAME/KEY: CDS
<222> LOCATION: (4)..(366)

<400> SEQUENCE: 1 cat atg cac tat cac cat cac atc ccc aca gaa att ccc aca agt gca 48
Met His Tyr His His His Ile Pro Thr Glu Ile Pro Thr Ser Ala
1 5 10 15 ttg gtg aaa cgt acc ttg gca ctg ctt tct act cat cga act ctg ctg 96
Leu Val Lys Arg Thr Leu Ala Leu Leu Ser Thr His Arg Thr Leu Leu
20 25 30 ata gcc aat gag act ctg agg att cct gtt cct gta cat aaa aat cac 144
Ile Ala Asn Glu Thr Leu Arg Ile Pro Val Pro Val His Lys Asn His
35 40 45 caa ctg tgc act gaa gaa atc ttt cag gga ata ggc aca ctg gag agt 192
Gln Leu Cys Thr Glu Glu Ile Phe Gln Gly Ile Gly Thr Leu Glu Ser
50 55 60 caa act gtg caa ggg ggt act gtg gaa aga cta ttc aaa aac ttg tcc 240
Gln Thr Val Gln Gly Gly Thr Val Glu Arg Leu Phe Lys Asn Leu Ser
65 70 75 tta ata aag aaa tac att gac ggc cag aag aag aag tgt gga gaa gaa 288
Leu Ile Lys Lys Tyr Ile Asp Gly Gln Lys Lys Lys Cys Gly Glu Glu
80 85 90 95 cgt cgt cgt gta aac caa ttc ctg gac tac ctg caa gag ttt ctt ggt 336
Arg Arg Arg Val Asn Gln Phe Leu Asp Tyr Leu Gln Glu Phe Leu Gly
100 105 110 gta atg aac acc gaa tgg atc atc gaa tcc tgatgaagct t 377
Val Met Asn Thr Glu Trp Ile Ile Glu Ser
115 120

<210> SEQ ID NO 2
<211> LENGTH: 121
<212> TYPE: PRT
<213> ORGANISM: modified IL-5

<400> SEQUENCE: 2

Met His Tyr His His His Ile Pro Thr Glu Ile Pro Thr Ser Ala Leu
1 5 10 15

Val Lys Arg Thr Leu Ala Leu Leu Ser Thr His Arg Thr Leu Leu Ile
20 25 30

Ala Asn Glu Thr Leu Arg Ile Pro Val Pro Val His Lys Asn His Gln
35 40 45

Leu Cys Thr Glu Glu Ile Phe Gln Gly Ile Gly Thr Leu Glu Ser Gln
50 55 60

Thr Val Gln Gly Gly Thr Val Glu Arg Leu Phe Lys Asn Leu Ser Leu
65 70 75 80

Ile Lys Lys Tyr Ile Asp Gly Gln Lys Lys Lys Cys Gly Glu Glu Arg
85 90 95

Arg Arg Val Asn Gln Phe Leu Asp Tyr Leu Gln Glu Phe Leu Gly Val
100 105 110

Met Asn Thr Glu Trp Ile Ile Glu Ser
115 120

```
<210> SEQ ID NO 3
<211> LENGTH: 6
<212> TYPE: PRT
<213> ORGANISM: leader peptide

<400> SEQUENCE: 3

Met His Tyr His His His
 1               5

<210> SEQ ID NO 4
<211> LENGTH: 21
<212> TYPE: PRT
<213> ORGANISM: peptide
<220> FEATURE:
<221> NAME/KEY: PEPTIDE
<222> LOCATION: (7)
<223> OTHER INFORMATION: Xaa can be any amino acid

<400> SEQUENCE: 4

Thr Ser Ala Leu Val Lys Xaa Thr Leu Ala Leu Leu Ser Thr His Arg
 1               5                  10                  15

Thr Leu Leu Ile Ala
            20

<210> SEQ ID NO 5
<211> LENGTH: 21
<212> TYPE: PRT
<213> ORGANISM: peptide

<400> SEQUENCE: 5

Thr Ser Ala Leu Val Lys Lys Thr Leu Ala Leu Leu Ser Thr His Arg
 1               5                  10                  15

Thr Leu Leu Ile Ala
            20

<210> SEQ ID NO 6
<211> LENGTH: 21
<212> TYPE: PRT
<213> ORGANISM: peptide

<400> SEQUENCE: 6

Thr Ser Ala Leu Val Lys Arg Thr Leu Ala Leu Leu Ser Thr His Arg
 1               5                  10                  15

Thr Leu Leu Ile Ala
            20

<210> SEQ ID NO 7
<211> LENGTH: 21
<212> TYPE: PRT
<213> ORGANISM: peptide

<400> SEQUENCE: 7

Thr Ser Ala Leu Val Lys Gln Thr Leu Ala Leu Leu Ser Thr His Arg
 1               5                  10                  15

Thr Leu Leu Ile Ala
            20

<210> SEQ ID NO 8
<211> LENGTH: 21
<212> TYPE: PRT
<213> ORGANISM: peptide

<400> SEQUENCE: 8
```

-continued

```
Thr Ser Ala Leu Val Lys Asn Thr Leu Ala Leu Leu Ser Thr His Arg
 1               5                  10                  15
Thr Leu Leu Ile Ala
            20
```